(12) United States Patent
Greenwald

(10) Patent No.: US 8,536,199 B2
(45) Date of Patent: Sep. 17, 2013

(54) ORAL COMBINATION OF VITAMINS

(76) Inventor: Sarah Steinberg Greenwald, Jerusalem (IL)

(*) Notice: Subject to any disclaimer, the term of this patent is extended or adjusted under 35 U.S.C. 154(b) by 122 days.

(21) Appl. No.: 12/933,419

(22) PCT Filed: Mar. 19, 2009

(86) PCT No.: PCT/IL2009/000310
§ 371 (c)(1),
(2), (4) Date: Oct. 20, 2010

(87) PCT Pub. No.: WO2009/118726
PCT Pub. Date: Oct. 1, 2009

(65) Prior Publication Data
US 2011/0028436 A1      Feb. 3, 2011

Related U.S. Application Data

(60) Provisional application No. 61/064,750, filed on Mar. 25, 2008.

(51) Int. Cl.
*A61K 31/44*   (2006.01)
*A61K 31/34*   (2006.01)

(52) U.S. Cl.
USPC ............ 514/332; 514/474; 514/872; 514/904

(58) Field of Classification Search
USPC .................. 514/332, 474, 904, 872
See application file for complete search history.

(56) References Cited

U.S. PATENT DOCUMENTS 6,197,329 B1   3/2001   Hermelin et al.
2005/0256031 A1   11/2005   Hageman et al.

FOREIGN PATENT DOCUMENTS

DE   10238677 A1 *  3/2004

OTHER PUBLICATIONS

Machine Translation for German Patent 10238677 A1 (2004).*

* cited by examiner

*Primary Examiner* — Kevin E Weddington
(74) *Attorney, Agent, or Firm* — Pearl Cohen Zedek Latzer, LLP; Mark S. Cohen

(57) ABSTRACT

This invention provides compositions for treating and preventing nausea and other disorders, the compositions comprising vitamins as active ingredients, including vitamin B6, vitamin K, and vitamin C, and a method for treating nausea or morning sickness with the oral compositions.

30 Claims, No Drawings

ORAL COMBINATION OF VITAMINS

CROSS-REFERENCE TO RELATED APPLICATIONS

This application is a U.S. National Phase Application under 35 U.S.C. 371 of PCT International Application No. PCT/IL2009/000310, which has an international filing date of Mar. 19, 2009, and which claims priority from U.S. Provisional Patent Application No. 61/064,750, filed Mar. 25, 2008, all of which disclosures are hereby incorporated by reference.

FIELD OF INVENTION

This invention provides oral compositions comprising vitamins and a method for using same.

BACKGROUND OF THE INVENTION

Nausea is a reaction to a number of causes that include overeating, infection, or irritation of the throat or stomach lining. Persistent or recurrent nausea and vomiting should be checked by a doctor.

Persistent, unexplained, or recurring nausea and vomiting can be symptoms of a variety of illnesses. It can be caused by simply overeating or drinking too much alcohol. It can be due to stress, certain medications, or illness. For example, people who are given morphine or other opioid medications for pain relief after surgery sometimes feel nauseated by the drug. Such poisonous substances as arsenic and other heavy metals cause nausea and vomiting. Morning sickness is a consequence of pregnancy-related hormone changes. Motion sickness can be induced by traveling in a vehicle, plane, or on a boat. Many patients experience nausea after eating spoiled food or foods to which they are allergic. Patients who suffer migraine headache often experience nausea. Cancer patients on chemotherapy are often nauseated. Gallstones, gastroenteritis, and stomach ulcer may cause nausea and vomiting. Such infectious illnesses as dengue fever and severe acute respiratory syndrome (SARS) may be accompanied by nausea and vomiting.

Vitamin K is a fat-soluble vitamin. The recommended dietary allowance (RDA) for vitamin K is 80 mg/day for the adult man, 65 mg/day for the adult woman, and 5 mg/day for the newborn infant. The vitamin K present in plant foods is called phylloquinone; while the form of the vitamin present in animal foods is called menaquinone. Both of these vitamins are absorbed from the diet and converted to an active form called dihydrovitamin K.

Vitamin K plays an important role in blood clotting. Without the vitamin, even a small cut would cause continuous bleeding in the body, and death. Blood clotting is a process that begins automatically when any injury produces a tear in a blood vessel. The process of blood clotting involves a collection of molecules, which circulate continuously through the bloodstream. When an injury occurs, these molecules rapidly assemble and form the blood clot. The clotting factors are proteins, and include proteins called Factor II, Factor VII, Factor IX, and Factor X. Factor II is also called prothrombin. These proteins require vitamin K for their synthesis in the body. The blood-clotting process also requires a dozen other proteins that do not need vitamin K for their synthesis.

SUMMARY OF THE INVENTION

This invention provides, in one embodiment, a composition comprising vitamins as active ingredients, wherein the active ingredients consist 10 to 80 mg vitamin B6, 1-10 mcg vitamin K, and 2-300 mg vitamin C, wherein the composition is in an oral dosage form.

In another embodiment, the present invention provides a method for preventing nausea in a subject comprising administering orally to a subject a composition comprising vitamin B6, vitamin K, and vitamin C, thereby preventing nausea in a subject In another embodiment, the present invention provides a method for inhibiting nausea in a subject comprising administering orally to a subject a composition comprising vitamin B6, vitamin K, and vitamin C, thereby inhibiting nausea in a subject.

In another embodiment, the present invention provides a method for reducing the symptoms associated with nausea in a subject comprising administering orally to a subject a composition comprising vitamin B6, vitamin K, and vitamin C, thereby inhibiting nausea in a subject.

In another embodiment, the present invention provides a method for treating nausea in a subject comprising administering orally to a subject a composition comprising vitamin B6, vitamin K, and vitamin C, thereby inhibiting nausea in a subject

DETAILED DESCRIPTION OF THE INVENTION

This invention provides compositions and methods comprising vitamin B6, vitamin K, and vitamin C. In another embodiment, this invention provides oral dosage forms comprising a composition which comprises vitamin B6, vitamin K, and vitamin C.

In another embodiment, vitamin B6 comprises 3-hydroxy-2-methyl-pyrimidine derivatives. In another embodiment, vitamin B6 is pyridoxine (PN). In another embodiment, vitamin B6 comprises the derivative pyridoxal (PL). In another embodiment, vitamin B6 comprises the derivative pyridoxamine (PM). In another embodiment, vitamin B6 comprises the derivative pyridoxine 5'-phosphate (PNP). In another embodiment, vitamin B6 comprises the derivative pyridoxal 5'-phosphate (PLP). P In another embodiment, vitamin B6 comprises the derivative pyridoxamine 5'-phosphate (PMP).

In another embodiment, vitamin C comprises the L-enantiomer of ascorbate. In some embodiments, vitamin C of the present invention derives from meat. In another embodiment, vitamin C of the present invention derives from liver. In some embodiments, vitamin C of the present invention derives from fruits or vegetables. In another embodiment, vitamin C of the present invention derives from camu camu fruit. In another embodiment, vitamin C of the present invention derives from billygoat plum. In another embodiment, vitamin C of the present invention derives from Wolfberry. In another embodiment, vitamin C of the present invention derives from Rose hip. In another embodiment, vitamin C of the present invention derives from acerola. In another embodiment, vitamin C of the present invention derives from amla. In another embodiment, vitamin C of the present invention derives from jujube. In another embodiment, vitamin C of the present invention derives from baobab. In another embodiment, vitamin C of the present invention derives from blackcurrant. In another embodiment, vitamin C of the present invention derives from red pepper. In another embodiment, vitamin C of the present invention derives from parsley. In another embodiment, vitamin C of the present invention derives from seabuckthorn. In another embodiment, vitamin C of the present invention derives from guava. In another embodiment, vitamin C of the present invention derives from kiwi. In another embodiment, vitamin C of the present invention derives from broccoli. In another embodiment, vitamin C of the present invention derives from longanberry. Each possibility represents a separate embodiment of the present invention.

In another embodiment, vitamin C as ascorbic acid is in the form of crystals. In another embodiment, vitamin C is in the form of various mineral ascorbates.

In another embodiment, vitamin C of the present invention is produced from glucose by two main routes. In another embodiment, the Reichstein process is used. In some embodiments, a two-step fermentation process is used. In another embodiment, the processes at least 40% vitamin C from the glucose feed. In another embodiment, the processes at least 50% vitamin C from the glucose feed. In another embodiment, the processes at least 60% vitamin C from the glucose feed. In another embodiment, the processes at least 70% vitamin C from the glucose feed. Each possibility represents a separate embodiment of the present invention.

In another embodiment, vitamin K of the present invention is a 2-methyl-1,4-naphthoquinone derivative. In another embodiment, vitamin K of the present invention is vitamin K2 (menaquinone, menatetrenone). In another embodiment, vitamin K of the present invention is phylloquinone (also known as vitamin K1).

In another embodiment, vitamin K of the present invention is produced from leafy green vegetables. In another embodiment, vitamin K of the present invention is produced from spinach. In another embodiment, vitamin K of the present invention is produced from kale. In another embodiment, vitamin K of the present invention is produced from Brassica. In another embodiment, vitamin K of the present invention is produced from cabbage. In another embodiment, vitamin K of the present invention is produced from cauliflower. In another embodiment, vitamin K of the present invention is produced from broccoli. In another embodiment, vitamin K of the present invention is produced from brussels sprouts. In another embodiment, vitamin K of the present invention is produced from avocado. In another embodiment, vitamin K of the present invention is produced from kiwifruit.

In another, embodiment, the active ingredients of the composition of the present invention consist vitamins. In another, embodiment, the active ingredients of the composition of the present invention consist vitamin B6, vitamin K, and vitamin C.

In another, embodiment, the composition of the present invention comprises 1 to 150 mg vitamin B6. In another, embodiment, the composition of the present invention comprises 1 to 10 mg vitamin B6. In another, embodiment, the composition of the present invention comprises 5 to 15 mg vitamin B6. In another, embodiment, the composition of the present invention comprises 10 to 80 mg vitamin B6. In another, embodiment, the composition of the present invention comprises 20 to 30 mg vitamin B6. In another, embodiment, the composition of the present invention comprises 30 to 60 mg vitamin B6. In another, embodiment, the composition of the present invention comprises 50 to 70 mg vitamin B6. In another, embodiment, the composition of the present invention comprises 60 to 90 mg vitamin B6. In another, embodiment, the composition of the present invention comprises 70 to 100 mg vitamin B6. In another, embodiment, the composition of the present invention comprises 80 to 11200 mg vitamin B6. In another, embodiment, the composition of the present invention comprises 120 to 150 mg vitamin B6.

In another, embodiment, the composition of the present invention comprises 0.5-30 mcg vitamin K. In another, embodiment, the composition of the present invention comprises 1-3 mcg vitamin K. In another, embodiment, the composition of the present invention comprises 2-4 mcg vitamin K. In another, embodiment, the composition of the present invention comprises 3-6 mcg vitamin K. In another, embodiment, the composition of the present invention comprises 5-8 mcg vitamin K. In another, embodiment, the composition of the present invention comprises 8-10 mcg vitamin K. In another, embodiment, the composition of the present invention comprises 10-12 mcg vitamin K. In another, embodiment, the composition of the present invention comprises 12-15 mcg vitamin K. In another, embodiment, the composition of the present invention comprises 15-20 mcg vitamin K. In another, embodiment, the composition of the present invention comprises 20-25 mcg vitamin K. In another, embodiment, the composition of the present invention comprises 25-30 mcg vitamin K.

In another, embodiment, the composition of the present invention comprises 0.5-15 mg vitamin K. In another, embodiment, the composition of the present invention comprises 1-3 mg vitamin K. In another, embodiment, the composition of the present invention comprises 2-4 mg vitamin K. In another, embodiment, the composition of the present invention comprises 3-6 mg vitamin K. In another, embodiment, the composition of the present invention comprises 5-8 mg vitamin K. In another, embodiment, the composition of the present invention comprises 4-10 mg vitamin K. In another, embodiment, the composition of the present invention comprises 4-6 mg vitamin K. In another, embodiment, the composition of the present invention comprises 8-12 mg vitamin K. In another, embodiment, the composition of the present invention comprises 12-15 mg vitamin K. In another, embodiment, the composition of the present invention comprises 8-15 mg vitamin K. In another, embodiment, the composition of the present invention comprises 5-12 mg vitamin K.

In another, embodiment, the composition of the present invention comprises 1-500 mg vitamin C. In another, embodiment, the composition of the present invention comprises 2-300 mg vitamin C. In another, embodiment, the composition of the present invention comprises 2-50 mg vitamin C. In another, embodiment, the composition of the present invention comprises 30-80 mg vitamin C. In another, embodiment, the composition of the present invention comprises 50-100 mg vitamin C. In another, embodiment, the composition of the present invention comprises 75-150 mg vitamin C. In another, embodiment, the composition of the present invention comprises 150-250 mg vitamin C. In another, embodiment, the composition of the present invention comprises 200-300 mg vitamin C. In another, embodiment, the composition of the present invention comprises 250-300 mg vitamin C. In another, embodiment, the composition of the present invention comprises 250-400 mg vitamin C. In another, embodiment, the composition of the present invention comprises 250-350 mg vitamin C. In another, embodiment, the composition of the present invention comprises 300-500 mg vitamin C. In another, embodiment, the composition of the present invention comprises 350-500 mg vitamin C. In another, embodiment, the composition of the present invention comprises 400-500 mg vitamin C.

In another, embodiment, the composition of the present invention further comprises choline. In another, embodiment, the composition of the present invention further comprises lecithin as a source for choline. In another, embodiment, choline of the present invention is derived from soy. In another, embodiment, choline of the present invention is derived from egg yolks. In another, embodiment, choline of the present invention is phosphatidylcholine. In another, embodiment, choline of the present invention is choline chloride.

In another, embodiment, the composition of the present invention further comprises 1-300 mg choline. In another, embodiment, the composition of the present invention further comprises 1-10 mg choline. In another, embodiment, the composition of the present invention further comprises 5-20 mg choline. In another, embodiment, the composition of the present invention further comprises 10-30 mg choline. In another, embodiment, the composition of the present invention further comprises 20-60 mg choline. In another, embodiment, the composition of the present invention further comprises 50-80 mg choline. In another, embodiment, the composition of the present invention further comprises 70-150 mg choline. In another, embodiment, the composition of the present invention further comprises 80-120 mg choline. In another, embodiment, the composition of the present invention further comprises 100-200 mg choline. In another, embodiment, the composition of the present invention further comprises 120-180 mg choline. In another, embodiment, the composition of the present invention further comprises 150-220 mg choline. In another, embodiment, the composition of the present invention further comprises 180-300 mg choline. In another, embodiment, the composition of the present invention further comprises 230-300 mg choline. In another, embodiment, the composition of the present invention further comprises 250-300 mg choline.

In another, embodiment, the composition of the present invention further comprises methionine. In another, embodiment, methionine is a racemic methionine. In another, embodiment, methionine is synthesized from diethyl sodium phthalimidomalonate by alkylation with chloroethylmethylsulfide followed by hydrolysis and decarboxylation.

In another, embodiment, methionine of the present invention is derived from a seed. In another, embodiment, methionine of the present invention is derived from Brazil nuts.

In another, embodiment, the composition of the present invention further comprises 20-300 mg methionine. In another, embodiment, the composition of the present invention further comprises 20-50 mg methionine. In another, embodiment, the composition of the present invention further comprises 40-80 mg methionine. In another, embodiment, the composition of the present invention further comprises 50-100 mg methionine. In another, embodiment, the composition of the present invention further comprises 75-125 mg methionine. In another, embodiment, the composition of the present invention further comprises 120-200 mg methionine. In another, embodiment, the composition of the present invention further comprises 150-250 mg methionine. In another, embodiment, the composition of the present invention further comprises 180-300 mg methionine. In another, embodiment, the composition of the present invention further comprises 250-300 mg methionine.

In another, embodiment, the composition of the present invention further comprises L-methionine. In another, embodiment, the composition of the present invention further comprises 50-500 mg L-methionine. In another, embodiment, the composition of the present invention further comprises 50-70 mg L-methionine. In another, embodiment, the composition of the present invention further comprises 50-80 mg L-methionine. In another, embodiment, the composition of the present invention further comprises 50-100 mg L-methionine. In another, embodiment, the composition of the present invention further comprises 75-125 mg L-methionine. In another, embodiment, the composition of the present invention further comprises 120-200 mg L-methionine. In another, embodiment, the composition of the present invention further comprises 150-250 mg L-methionine. In another, embodiment, the composition of the present invention further comprises 180-300 mg L-methionine. In another, embodiment, the composition of the present invention further comprises 250-300 mg L-methionine. In another, embodiment, the composition of the present invention further comprises 250-400 mg L-methionine. In another, embodiment, the composition of the present invention further comprises 300-450 mg L-methionine. In another, embodiment, the composition of the present invention further comprises 400-450 mg L-methionine. In another, embodiment, the composition of the present invention further comprises 450-500 mg L-methionine.

In another embodiment, the composition of the present invention is in a chewable oral dosage form. In another embodiment, the chewable oral dosage form is a chewable tablet. In another embodiment, the chewable tablet of the invention is taken slowly by chewing or sucking in the mouth. In another embodiment, the chewable tablet of the invention enables the vitamins contained therein to be orally administered without drinking.

In another embodiment of the present invention, the composition further comprises fructose, sorbitol, microcrystalline cellulose, magnesium stearate, or any combination thereof. In another embodiment, the composition further comprises chamomile. In another embodiment, the composition further comprises ginger. In another embodiment, the composition further comprises peppermint. In another embodiment, the composition further comprises anise. In another embodiment, the composition further comprises fennel. In another embodiment, the composition further comprises thyme. In another embodiment, the composition further comprises Arsenicum album. In another embodiment, the composition further comprises Carbo vegetabilis. In another embodiment, the composition further comprises Ignatia, homeopathic ipecac. In another embodiment, the composition further comprises Nux vomica. In another embodiment, the composition further comprises Zingiber officinale.

In another embodiment, the composition of the present invention is in the form of a chewing gum product. In another embodiment, chewing gum compositions contemplated by the present invention comprise all types of sugar and sugarless chewing gums and chewing gum formulations known to those skilled in the art, including regular and bubble gum types. In another embodiment, chewing gum compositions of the invention comprise a chewing gum base, a modifier, a bulking agent or sweetener, and one or more other additives such as, flavoring agents, colorants and antioxidants. In another embodiment, the modifying agents are used to soften, plasticize and/or compatibilize one or more of the components of the gum base and/or of the formulation as a whole.

In another embodiment, the present invention provides a soft, chewable dosage form which is pliable and chewy, yet dissolves quickly in the mouth, has a long shelf life, contains little moisture which improves stability and decreases the tendency for the dosage form to dry out, does not require cooking or heating as part of the manufacturing process. In another embodiment, the dosage form is used as a matrix for vitamins.

In another embodiment, the chewable tablet of the invention comprises a metal salt such as calcium, magnesium, aluminum salt, or any mixture thereof. In another embodiment, the chewable tablet of the invention comprises hydroxyalkyl cellulose. In another embodiment, the chewable tablet of the invention comprises low viscosity hydroxyalkyl cellulose. In another embodiment, the chewable tablet of the invention comprises high viscosity hydroxyalkyl cellulose.

In another embodiment, the chewable tablet of the invention comprises various additives. In another embodiment, the chewable tablet of the invention comprises sweeteners. In another embodiment, the chewable tablet of the invention comprises acidic ingredients. In another embodiment, the chewable tablet of the invention comprises taste correctives. In another embodiment, the chewable tablet of the invention comprises polymeric compounds. In another embodiment, the chewable tablet of the invention comprises essential oils.

In another embodiment, the chewable tablet of the invention is a soft tablet. In another embodiment, the chewable tablet of the invention is made in a state of soft candy. In another embodiment, the chewable tablet of the invention is made in a state of jelly.

In another embodiment, the chewable tablet of the invention comprises a core comprising the vitamins of the invention. In another embodiment, the chewable tablet of the invention comprises an outer layer wrapping the core which is made up of chewable base such as a gum, a soft candy or a caramel.

In another embodiment, the chewable tablet of the invention protects the vitamins that are liable to transform. In another embodiment, the chewable tablet of the invention comprises pectin. In another embodiment, the chewable tablet of the invention comprises maltitol. In another embodiment, the chewable tablet of the invention comprises isomalt. In another embodiment, the chewable tablet of the invention comprises liquid glucose. In another embodiment, the chewable tablet of the invention comprises sugar. In another embodiment, the chewable tablet of the invention comprises citric acid. In another embodiment, the chewable tablet of the invention comprises sorbitol. In another embodiment, the chewable tablet of the invention comprises a flavoring agent. In another embodiment, the chewable tablet of the invention comprises a natural flavoring agent. In another embodiment, the chewable tablet of the invention comprises a synthetic flavor. In another embodiment, the chewable tablet of the invention comprises a volatile oil. In another embodiment, the chewable tablet of the invention comprises synthetic flavor oil. In another embodiment, the chewable tablet of the invention comprises a flavoring aromatic. In another embodiment, the chewable tablet of the invention comprises a oleoresin. In another embodiment, the chewable tablet of the invention comprises an extract derived from a plant. In another embodiment, the chewable tablet of the invention comprises an extract derived from a leaf. In another embodiment, the chewable tablet of the invention comprises an extract derived from a flower. In another embodiment, the chewable tablet of the invention comprises an extract derived from a fruit. In another embodiment, the chewable tablet of the invention comprises an extract derived from a stem.

In another embodiment, the chewable tablet of the invention comprises citrus oil such as but not limited to lime, grapefruit, lemon, or orange. In another embodiment, the chewable tablet of the invention comprises fruit essences such as but not limited to apple, pear, peach, grape, strawberry, raspberry, cherry, plum, pineapple, apricot or other fruit flavors. In another embodiment, the chewable tablet of the invention comprises flavorings such as but not limited to aldehydes and esters such as benzaldehyde (cherry, almond), citral, i.e., alphacitral (lemon, lime), neral, i.e., beta-citral (lemon, lime) decanal (orange, lemon), aldehyde C-8 (citrus fruits), aldehyde C-9 (citrus fruits), adlehyde C-12 (citrus fruits), tolyl aldehyde (cherry, almond), 2,6-dimethyloctanal (green fruit), and 2-dodecenal (citrus, mandarin), mixtures thereof and the like.

In another embodiment, the chewable tablet of the invention comprises a gum. In another embodiment, the chewable tablet of the invention comprises a soft gum. In another embodiment, the chewable tablet of the invention comprises nougat. In another embodiment, the chewable tablet of the invention comprises soft candy. In another embodiment, the chewable tablet of the invention comprises hard candy. In another embodiment, the chewable tablet of the invention comprises caramel. In another embodiment, the chewable tablet of the invention comprises an enhancing agent of chewing property.

In another embodiment, sugar used in the present invention may be selected from the group consisting of white sugar, liquid glucose, sorbitol, dextrose, isomalt, liquid maltitol, aspartame and lactose, and this sugar may comprise 30-90 weight % by total weight of the ingredients.

In another embodiment, the chewable tablet of the invention comprises a sweetener such as but not limited to: glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; *Stevia Rebaudiana* (Stevioside); chloro derivatives of sucrose such as suralose; sugar alcohols such as sorbitol, mannitol, xylitol, and the like. In another embodiment, the chewable tablet of the invention comprises hydrogenated starch hydrolysates and the synthetic sweetener 3,6-dihydro-6-methyl-1-1-1,2,3-oxathiazin-4-one-2,2-dioxide. In another embodiment, the chewable tablet of the invention comprises the potassium salt (acesulfame-K), and sodium and calcium salts of 3,6-dihydro-6-methyl-1-1-1,2,3-oxathiazin-4-one-2,2-dioxide. In another embodiment, the chewable tablet of the invention comprises other sweeteners known to one of skill in the art.

In another embodiment, glycerin, lecithin, hydrogenated palm oil or glyceryl monostearate are used as a protecting agent of crystallization of the sugars in 0.02-3.0 weight % by total weight of the ingredients, to prevent adhesion to oral cavity and improve the soft property of the products.

In another embodiment, isomalt or liquid maltitol are used as an enhancing agent of chewing property. In another embodiment, gelatin or arabic gum are used as a keeping agent of hardness and extension property in 0.1-3.0 weight % by total weight of the ingredients. In another embodiment, food flavor or a fruits extract; a souring agent such as citric acid are added in adequate amount. In another embodiment, a coloring agent such as a food color is optionally added in a small amount.

Yet a further embodiment of the present invention includes the use of an effervescent disintegration agent. In another embodiment, its action aids in the masking of objectionable taste of the vitamins.

In another embodiment, of the present invention the effervescent disintegration agent is an acid. In another embodiment, of the present invention the effervescent disintegration agent is citric acid. In another embodiment, of the present invention the effervescent disintegration agent is tartaric acid. In another embodiment, of the present invention the effervescent disintegration agent is malic acid. In another embodiment, of the present invention the effervescent disintegration agent is fumaric acid. In another embodiment, of the present invention the effervescent disintegration agent is adipic acid. In another embodiment, of the present invention the effervescent disintegration agent is succinic acid. In another embodiment, of the present invention the effervescent disintegration agent is at least one base such as but not limited to: carbonate salts, bicarbonate salts and mixtures thereof.

In another embodiment, the chewable tablet of the invention comprises a crystallization modifier such but not limited to, surfactants (Spans™ and Tweens™), dextrose, polyethylene glycol (PEG), polypropylene glycol (PPG), etc. These modifiers generally provide controlled acceleration of crystallization while the matrix is bound. In another embodiment, these crystallization modifiers enhance the formation of a crystalline frame and the conversion of the remaining mass.

In another embodiment, crystallization modifiers are surfactants having a hydrophilic to lipid balance (HLB) of six or greater, i.e., they have the same degree of hydrophilicity as surfactants characterized by degree of HLB. In another embodiment, such materials include, but are not limited to anionic, cationic and zwitterionic surfactants as well as neutral materials which have an HLB of six or greater. In another embodiment, crystallization modifiers are hydrophilic materials having polyethylene oxide linkages. In another embodiment, crystallization modifiers have a molecular weight of at least 100.

In another embodiment, the chewable tablet of the invention comprises a filler. In another embodiment, filler increases the bulk of the tablet. In another embodiment, the filler is calcium sulfate, both di- and tri basic, starch, calcium carbonate, microcrystalline cellulose, modified starches, lactose, sucrose, mannitol, sorbitol, or any combination thereof.

In another embodiment, the chewable tablet of the invention comprises a binder such as but not limited to: starches, pregelatinize starches, gelatin, polyvinylpyrrolidone, methylcellulose, sodium carboxymethylcellulose, ethylcellulose, polyacrylamides, polyvinyloxoazolidone, and polyvinylalcohols.

In another embodiment, the chewable tablet of the invention comprises a lubricant such as but not limited to: magnesium stearate, calcium stearate, zinc stearate, hydrogenated vegetable oils, sterotex, polyoxyethylene, monostearate, talc, polyethyleneglycol, sodium benzoate, sodium lauryl sulfate, magnesium lauryl sulfate and light mineral oil.

In another embodiment, the chewable tablet of the invention comprises a dispersion enhancer such as but not limited to: starch, alginic acid, polyvinylpyrrolidones, guar gum, partially hydrolyzed guar gum, kaolin, bentonite, purified wood cellulose, sodium starch glycolate, isomorphous silicate, and microcrystalline cellulose as high HLB emulsifier surfactants.

In another embodiment, the chewable tablet of the invention comprises a disintegrant such as but not limited to: Croscarmellose sodium, marketed under the trade name Ac-Di-Sol.

In another embodiment, the chewable tablet of the invention comprises an absorbent such as but not limited to: maltodextrin. In another embodiment, the chewable tablet of the invention comprises an emulsifier such as but not limited to: Mono- and diglycerides, Oleaginous substances such as food oils like Medium, Chain Triglycerides (MCT), and Stearine D 17.

In another embodiment, the chewable tablet of the invention comprises a water soluble bulking agent such as but not limited to: hydrocolloid thickeners and binders, such as gum arabic, pectins, modified starches, alginates, carrageenans, xanthan gums, carboxymethylcellulose, methylcellulose, hydroxyethylcellulose, hydroxypropylcellulose, hydroxypropylmethylcellulose, propylene glycol alginate, polyvinylpyrrolidone (PVP), carboxyvinyl polymers (such as Carbopol®), polyethylene oxide polymers (such as Polyox®), sorbitol, xylitol, sucrose, fructose, dextrose, mannitol, starch maltodextrin, corn syrup solids, or combinations thereof.

In another embodiment, the chewable tablet of the invention comprises a water insoluble bulking agent such as but not limited to: talc, dicalcium phosphate, powdered celluloses, microcrystalline celluloses and antacid compounds.

In another embodiment, the chewable tablet of the invention comprises vitamins in compressed particles. In another embodiment, individual particles are coated with a blend of cellulose acetate or cellulose acetate butyrate and polyvinyl pyrrolidone (USP Povidone or "PVP"). In another embodiment, the coating provides excellent taste masking while still permitting acceptable bioavailability of the vitamins. In another embodiment, the chewable tablet In another embodiment, the invention relates to a composition of the invention comprised within chewable and edible soft gelatin capsules, the shells of which comprise gelatin, water, plasticizer and a hydrogenated starch hydrolysate. In another embodiment, soft gelatin shell comprises about 10-45% gelatin; about 5-30% water; about 12-35% plasticizer; and about 2-25% of a hydrogenated starch hydrolysate. In another embodiment, the shell encloses a soft gelatin capsule fill material. In another embodiment, the gelatin may be of Type A, Type B, or a mixture thereof. In another embodiment, in order to augment the taste and chewability of the capsule shell, as well as to assist in the rapid dissolution of the shell upon chewing, the present capsule shell further comprises a hydrogenated starch hydrolysate.

In another embodiment, chewable systems of the invention are preferable for administering the vitamins of the invention. In another embodiment, the act of chewing increases the surface area of the vitamins and increases the rate of absorption by the digestive tract. In another embodiment, chewable systems of the invention provide vitamin, topically to the mouth or throat areas for both local effects and systemic absorption.

In another embodiment, the present invention provides a method for preventing nausea in a subject comprising administering orally to a subject a composition comprising vitamin B6, vitamin K, and vitamin C, thereby preventing nausea in a subject. In another embodiment, the present invention provides a method for preventing morning sickness in a subject comprising administering orally to a subject a composition comprising vitamin B6, vitamin K, and vitamin C, thereby preventing nausea in a subject. In another embodiment, the present invention provides a method for preventing morning sickness in a woman comprising administering orally to a subject a composition comprising vitamin B6, vitamin K, and vitamin C, thereby preventing nausea in a subject.

In another embodiment, the present invention provides that the symptoms of morning sickness include vomiting. In another embodiment, the present invention provides that morning sickness occurs at any time throughout the day. In another embodiment, the present invention provides that some women experience morning sickness for a short period of time, while others experience morning sickness throughout their entire pregnancy.

In another embodiment, the present invention provides a method for preventing nausea in a subject comprising administering orally to a subject a composition of the invention. In another embodiment, the present invention provides a method for preventing nausea in a subject comprising administering orally to a subject an oral dosage form comprising the composition of the invention. In another embodiment, the present invention provides a method for preventing nausea in a subject comprising administering orally to a subject a chewable oral dosage form comprising the composition of the invention. In another embodiment, the present invention provides a method for preventing nausea in a subject comprising administering orally to a subject a composition comprising 10 to 80 mg vitamin B6, 1-10 mcg vitamin K, and 2-300 mg vitamin C, thereby preventing nausea in a subject. In another embodiment, the composition further comprises 5-300 mg choline. In another embodiment, the composition further comprises 50-200 mg methionine. In another embodiment, the composition further comprises 100-400 mg L-methionine.

In another embodiment, the present invention provides a method for preventing nausea in a subject comprising administering orally to a subject a composition comprising 10 to 40 mg vitamin B6, 1-5 mcg vitamin K, and 2-100 mg vitamin C, thereby preventing nausea in a subject. In another embodiment, the composition further comprises 5-50 mg choline. In another embodiment, the composition further comprises 50-100 mg methionine. In another embodiment, the composition further comprises 100-200 mg L-methionine.

In another embodiment, the present invention provides that a method for preventing nausea in a subject differs from a method for treating nausea in a subject in the amount of vitamins in the composition. In another embodiment, the present invention provides that a method for preventing nausea in a subject comprises reduced amount of vitamins compared to the amount of vitamins administered in a composition for treating nausea in a subject.

In another embodiment, the present invention provides that nausea is the sensation of having a queasy stomach or being about to vomit. In another embodiment, the present invention provides that nausea occurs after eating rich or spoiled food. In another embodiment, the present invention provides that nausea occurs after taking a medication. In another embodiment, the present invention provides that nausea occurs after taking a new medication. In another embodiment, the present invention provides that nausea occurs after taking a chemotherapeutic medication. In another embodiment, the present invention provides that nausea is associated with dizziness.

In another embodiment, the present invention provides that nausea is caused by an unknown factor. In another embodiment, the present invention provides that nausea is caused by overeating. In another embodiment, the present invention provides that nausea is caused by drinking too much alcohol. In another embodiment, the present invention provides that nausea is caused due to stress. In another embodiment, the present invention provides that nausea is caused by morphine. In another embodiment, the present invention provides that nausea is caused by an opioid medication. In another embodiment, the present invention provides that nausea is caused by arsenic. In another embodiment, the present invention provides that nausea is caused by a heavy metal. In another embodiment, the present invention provides that nausea comprises motion sickness.

In another embodiment, the present invention provides that nausea comprises morning sickness. In another embodiment, the present invention provides that morning sickness is a consequence of pregnancy-related hormone changes. In another embodiment, the invention provides that compositions of the invention prevent, treat, inhibit, and reduce the symptoms associated with morning sickness.

In another embodiment, the present invention provides that nausea is diagnosed by one skilled in the art. In another embodiment, the present invention provides that diagnosis is based on the severity, frequency, and duration of symptoms.

In another embodiment, the subject is afflicted with cancer. In another embodiment, the subject is afflicted with an autoimmune disease. In another embodiment, the subject is afflicted with HIV. In another embodiment, the subject is a pregnant female. In another embodiment, the pregnant female is in her first trimester of pregnancy.

In another embodiment, the subject is a pregnant female afflicted with morning sickness. In another embodiment, the subject is a pregnant female with a high intake of saturated fat.

In another embodiment, the present invention provides a method for inhibiting nausea in a subject comprising administering orally to a subject a composition comprising vitamin B6, vitamin K, and vitamin C, thereby preventing nausea in a subject. In another embodiment, the present invention provides a method for inhibiting morning sickness in a subject comprising administering orally to a subject a composition comprising vitamin B6, vitamin K, and vitamin C, thereby inhibiting nausea in a subject. In another embodiment, the present invention provides a method for inhibiting morning sickness in a woman comprising administering orally to a subject a composition comprising vitamin B6, vitamin K, and vitamin C, thereby preventing nausea in a subject.

In another embodiment, the present invention provides a method for inhibiting nausea in a subject comprising administering orally to a subject a composition of the invention. In another embodiment, the present invention provides a method for inhibiting nausea in a subject comprising administering orally to a subject an oral dosage form comprising the composition of the invention.

In another embodiment, the present invention provides a method for inhibiting nausea in a subject comprising administering orally to a subject a composition of the invention In another embodiment, the present invention provides a method for inhibiting nausea in a subject comprising administering orally to a subject a chewable oral dosage form comprising the composition of the invention. In another embodiment, the present invention provides a method for inhibiting nausea in a subject comprising administering orally to a subject a composition comprising 10 to 80 mg vitamin B6, 1-10 mcg vitamin K, and 2-300 mg vitamin C, thereby inhibiting nausea in a subject. In another embodiment, the composition further comprises 5-300 mg choline. In another embodiment, the composition further comprises 50-200 mg methionine. In another embodiment, the composition further comprises 100-400 mg L-methionine.

In another embodiment, the subject is afflicted with cancer. In another embodiment, the subject is afflicted with an autoimmune disease. In another embodiment, the subject is afflicted with HIV. In another embodiment, the subject is a pregnant female. In another embodiment, the pregnant female is in her first trimester of pregnancy.

In another embodiment, the subject is a pregnant female afflicted with morning sickness. In another embodiment, the subject is a pregnant female with a high intake of saturated fat.

In another embodiment, the present invention provides a method for treating nausea in a subject comprising administering orally to a subject a composition of the invention. In another embodiment, the present invention provides a method for treating nausea in a subject comprising administering orally to a subject a chewable oral dosage form comprising the composition of the invention. In another embodiment, the present invention provides a method for treating nausea in a subject comprising administering orally to a subject a composition comprising 10 to 80 mg vitamin B6, 1-10 mcg vitamin K, and 2-300 mg vitamin C, thereby treating nausea in a subject. In another embodiment, the composition further comprises 5-300 mg choline. In another embodiment, the composition further comprises 50-200 mg methionine. In another embodiment, the composition further comprises 100-400 mg L-methionine.

In another embodiment, the subject is afflicted with cancer. In another embodiment, the subject is afflicted with an autoimmune disease. In another embodiment, the subject is afflicted with HIV. In another embodiment, the subject is a pregnant female. In another embodiment, the pregnant female is in her first trimester of pregnancy.

In another embodiment, the subject is a pregnant female afflicted with morning sickness. In another embodiment, the subject is a pregnant female with a high intake of saturated fat.

In another embodiment, the present invention provides a method for reducing the symptoms associated with nausea in a subject comprising administering orally to a subject a composition of the invention. In another embodiment, the present invention provides a method for reducing the symptoms associated with nausea in a subject comprising administering orally to a subject a composition comprising vitamin B6, vitamin K, and vitamin C, thereby inhibiting nausea in a subject. In another embodiment, the present invention provides a method for reducing the symptoms associated with nausea in a subject comprising administering orally to a subject a composition comprising 10 to 80 mg vitamin B6, 1-10 mcg vitamin K, and 2-300 mg vitamin C, thereby treating nausea in a subject. In another embodiment, the composition further comprises 5-300 mg choline. In another embodiment, the composition further comprises 50-200 mg methionine. In another embodiment, the composition further comprises 100-400 mg L-methionine.

In another embodiment, symptoms associated with nausea comprise dizziness, vomiting, retching, bloating, early satiety, dysphagia, odynophagia, lightheadedness, abdominal or chest pain, cough, vertigo, arthralgias, low grade fevers, chills, or any combination thereof.

In another embodiment, the methods of the present invention can treat, inhibit, prevent, or reduce the symptoms associated with acute nausea and vomiting. In another embodiment, the methods of the present invention can treat, inhibit, prevent, or reduce the symptoms associated with pregnancy-related nausea and vomiting. In another embodiment, the methods of the present invention can treat, inhibit, prevent, or reduce the symptoms associated with nausea and vomiting induced by vestibular neuronitis. In another embodiment, the methods of the present invention can treat, inhibit, prevent, or reduce the symptoms associated with nausea and vomiting induced by acute labyrinthitis. In another embodiment, the methods of the present invention can treat, inhibit, prevent, or reduce the symptoms associated with nausea and vomiting induced by Meniere's disease. In another embodiment, the methods of the present invention can treat, inhibit, prevent, or reduce the symptoms associated with nausea and vomiting induced by motion sickness. In another embodiment, the methods of the present invention can treat, inhibit, prevent, or reduce the symptoms associated with nausea and vomiting induced by viral syndrome. In another embodiment, the methods of the present invention can treat, inhibit, prevent, or reduce the symptoms associated with post-operative nausea and vomiting. In another embodiment, the methods of the present invention can treat, inhibit, prevent, or reduce the symptoms associated with nausea and vomiting induced by drug, toxin or environmental exposure. In another embodiment, the methods of the present invention can treat, inhibit, prevent, or reduce the symptoms associated with nausea and vomiting induced by chemotherapeutic agents. In another embodiment, the methods of the present invention can treat, inhibit, prevent, or reduce the symptoms associated with nausea and vomiting induced by drugs. In another embodiment, the methods of the present invention can treat, inhibit, prevent, or reduce the symptoms associated with nausea and vomiting induced by alcohol. In another embodiment, the methods of the present invention can treat, inhibit, prevent, or reduce the symptoms associated with nausea and vomiting induced by organic solvents. In another embodiment, the methods of the present invention can treat, inhibit, prevent, or reduce the symptoms associated with nausea and vomiting induced by high altitude illness. In another embodiment, the methods of the present invention can treat, inhibit, prevent, or reduce the symptoms associated with nausea and vomiting induced by Hyperemesis gravidarum. In another embodiment, the methods of the present invention can treat, inhibit, prevent, or reduce the symptoms associated with nausea and vomiting induced by HELLP Syndrome. In another embodiment, the methods of the present invention can treat, inhibit, prevent, or reduce the symptoms associated with infections as a cause of nausea and vomiting. In another embodiment, the methods of the present invention can treat, inhibit, prevent, or reduce the symptoms associated with a systemic disease as a cause of nausea and vomiting. In another embodiment, the methods of the present invention can treat, inhibit, prevent, or reduce the symptoms associated with nausea and vomiting induced by immunosuppression. In another embodiment, the methods of the present invention can treat, inhibit, prevent, or reduce the symptoms associated with chronic nausea and vomiting. In another embodiment, the methods of the present invention can treat, inhibit, prevent, or reduce the symptoms associated with GI tract obstruction. In another embodiment, the methods of the present invention can treat, inhibit, prevent, or reduce the symptoms associated with Central nervous system (CNS) causes of nausea and vomiting. In another embodiment, the methods of the present invention can treat, inhibit, prevent, or reduce the symptoms associated with nausea and vomiting induced by diabetes mellitus. In another embodiment, the methods of the present invention can treat, inhibit, prevent, or reduce the symptoms associated with nausea and vomiting induced by psychogenic causes.

In another embodiment, the subject is afflicted with cancer. In another embodiment, the subject is afflicted with an autoimmune disease. In another embodiment, the subject is afflicted with HIV. In another embodiment, the subject is a pregnant female. In another embodiment, the pregnant female is in her first trimester of pregnancy.

In another embodiment, the subject is a pregnant female afflicted with morning sickness. In another embodiment, the subject is a pregnant female with a high intake of saturated fat.

In another embodiment, the invention provides various strengths (dosages of the vitamins) of the composition described herein. In another embodiment, a subject is treated with the composition comprising the minimal strength (minimal dosage of vitamins) that can effectively treat, inhibit, prevent, or reduce the symptoms associated with nausea.

In another embodiment, compositions of the invention can be formulated in additional dosage forms. In another embodiment, solid carriers/diluents for use in methods and compositions of the present invention include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In another embodiment, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants. Each of the above excipients represents a separate embodiment of the present invention.

In some embodiments, the dosage forms of the present invention are formulated to achieve an immediate release profile, an extended release profile, or a delayed release profile. In some embodiments, the release profile of the composition is determined by using specific excipients that serve for example as binders, disintegrants, fillers, or coating materials. In one embodiment, the composition will be formulated to achieve a particular release profile as known to one skilled in the art.

In one embodiment, the composition is formulated as an oral dosage form. In one embodiment, the composition is a solid oral dosage form comprising tablets, chewable tablets, or capsules. In one embodiment the capsules are soft gelatin capsules.

In other embodiments, controlled- or sustained-release coatings utilized in methods and compositions of the present invention include formulation in lipophilic depots (e.g. fatty acids, waxes, oils).

The compositions also include, in another embodiment, incorporation of vitamins into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance. In another embodiment, particulate compositions of the vitamins are coated with polymers (e.g. poloxamers or poloxamines)

The preparation of pharmaceutical compositions that contain vitamins, for example by mixing, granulating, or tablet-forming processes, is well understood in the art. The vitamins are often mixed with excipients that are pharmaceutically acceptable and compatible with the active ingredient. For oral administration, the active ingredients of compositions of the present invention are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions.

In another embodiment, additional methods of administering the vitamins of the invention comprise injectable dosage forms. In another embodiment, the injectable is administered intraperitonealy. In another embodiment, the injectable is administered intramuscularly. In another embodiment, the injectable is administered intradermally. In another embodiment, the injectable is administered intravenously. Each possibility represents a separate embodiment of the present invention.

In another embodiment, the pharmaceutical compositions are administered by intravenous, intra-arterial, or intra-muscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In another embodiment, additional methods of administering the vitamins of the invention comprise solutions. In another embodiment, the solution is administered orally. In another embodiment, the solution is administered by infusion. In another embodiment, the solution is a solution for inhalation. Each possibility represents a separate embodiment of the present invention.

In another embodiment, the vitamins of the invention are administered throughout the course of a disease or a medical condition such as pregnancy. In another embodiment, the vitamins of the invention are administered during symptomatic (nausea, vomiting etc.) stages a disease or a medical condition such as pregnancy. In another embodiment, the vitamins of the invention are administered as a pre-treatment for prevention of symptoms of a disease or a medical condition such as pregnancy or symptoms of a certain treatment such as chemotherapy. In another embodiment, the vitamins of the invention are administered as a post-treatment for preventing relapse of the symptoms such as morning sickness, nausea, and/or vomiting. Each possibility represents a separate embodiment of the present invention.

In another embodiment, the pharmaceutical composition is administered as a suppository, for example a rectal suppository or a urethral suppository. In another embodiment, the pharmaceutical composition is administered by subcutaneous implantation of a pellet. In another embodiment, the pellet provides for controlled release of active compound agent over a period of time. Each possibility represents a separate embodiment of the present invention.

In other embodiments, pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs. Each possibility represents a separate embodiment of the present invention.

In another embodiment, parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs. Each possibility represents a separate embodiment of the present invention.

In another embodiment, the pharmaceutical compositions provided herein are controlled-release compositions, i.e. compositions in which the active compounds are released over a period of time after administration. Controlled- or sustained-release compositions include formulation in lipophilic depots (e.g. fatty acids, waxes, oils). In another embodiment, the composition is an immediate-release composition, i.e. a composition in which all the active compound is released immediately after administration. Each possibility represents a separate embodiment of the present invention.

In another embodiment, the pharmaceutical composition is delivered in a controlled release system. In another embodiment, the agents are administered using intravenous infusion, an implantable osmotic pump, a transdermal patch, liposomes, or other modes of administration. In another embodiment, a pump is used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials are used; e.g. in microspheres in or an implant. In yet another embodiment, a controlled release system is placed in proximity to the therapeutic target, thus requiring only a fraction of the systemic dose (see, e.g., Goodson, in Medical Applications of Controlled Release, supra, vol. 2, pp. 115-138 (1984); and Langer R, Science 249: 1527-1533 (1990). Each possibility represents a separate embodiment of the present invention.

The compositions also include, in another embodiment, incorporation of the active materials into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance. Each possibility represents a separate embodiment of the present invention.

Also included in the present invention are particulate compositions coated with polymers (e.g. poloxamers or poloxamines) and the compound coupled to antibodies directed against tissue-specific receptors, ligands or antigens or coupled to ligands of tissue-specific receptors. Each possibility represents a separate embodiment of the present invention.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications also increase, in another embodiment, the compound's solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound. Each possibility represents a separate embodiment of the present invention.

The preparation of pharmaceutical compositions that contain the vitamins of the invention are preformed, for example by mixing, granulating, or tablet-forming processes, is well understood in the art. The active therapeutic ingredient is often mixed with excipients that are pharmaceutically acceptable and compatible with the active ingredient. For oral administration, the active compounds are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the active compounds are converted into a solution, suspension, or emulsion, if desired with the substances customary and suitable for this purpose, for example, solubilizers or other substances.

Each of the above additives, excipients, formulations and methods of administration represents a separate embodiment of the present invention.

In one embodiment, the term "treating" refers to curing a disease. In another embodiment, "treating" refers to preventing a disease. In another embodiment, "treating" refers to reducing the incidence of a disease. In another embodiment, "treating" refers to ameliorating symptoms of a disease. In another embodiment, "treating" refers to inducing remission. In another embodiment, "treating" refers to slowing the progression of a disease.

EXPERIMENTAL DETAILS SECTION

Example 1

A Chewable Tablet for Treating Nausea

Materials and Experimental Methods

An effective chewable tablet for treating morning sickness in pregnant women was prepared. The active ingredients included:

vitamin B6: 75 mg vitamin C: 300 mg vitamin K: 5 mcg

The effective chewable tablet for treating morning sickness in pregnant women also contained 300 mg of choline.

Example 2

Minimal Effective Dose of Vitamins in a Chewable Tablet for Preventing or Reducing the Symptoms Associated with Morning Sickness A minimal effective dose of vitamins in a chewable tablet for preventing or reducing the symptoms associated with morning sickness was prepared. The active ingredients included: vitamin B6: 5 mg vitamin C: 5 mg vitamin K: 2 mcg The minimal effective dose of vitamins in a chewable tablet for preventing or reducing the symptoms associated with morning sickness in pregnant women also contained 10 mg of choline.

Example 3

A Process of Making a Chewable Tablet for Treating Nausea

Materials and Experimental Methods

Chewable tablets comprising the vitamins of the invention for treating nausea and/or morning sickness in pregnant women were prepared as follows:

Phase A: 51.57% w/w fructose powder, 34.88% w/w sorbitol granules, 1.5% w/w microcrystalline cellulose, 2% w/w magnesium stearate, 2% w/w lemon fresh flavor, 1.5% w/w citric acid, 0.05% w/w natural chlorophyll color. A homogenous powder blend of Phase A was obtained by mixing the ingredients of phase A.

Phase B: 3.7% w/w vitamin B6 (37 mg), 2.5% w/w vitamin C (25 mg), vitamin K 5 mcg. The ingredients of phase B were mixed with the homogenous powder blend of Phase A for 40 minutes.

Phase C: Chewable tablets were prepared in a tableting machine. Each tablet weighed about 1 g (±10%).

Experimental Results Section

Chewable tablets were prepared in accordance with the methodology described hereinabove in example 3.

Example 4

Treatment of "Morning Sickness" in Pregnant Women

A group of pregnant women were provided with the tablets, as prepared in Example 3, and were advised to take one to two tablets per day. Table 1 provides results of a sample of responses from women in the group.

TABLE 1

Effects of taking chewable tablets over time in pregnant women in first trimester

| Volunteer number | Number of tablets/day | Duration of use | Age of volunteer | Reported effects on nausea and vomiting |
|---|---|---|---|---|
| 1 | 2 | 5 weeks | 28 | Reduced nausea and vomiting |
| 2 | 1 | 4 months | 31 | Reduced nausea |
| 3 | 2 | 3 months | 27 | Reduced nausea, improved general feeling |
| 4 | 5<br>3<br>1 | 3 days<br>10 days<br>20 days | 24 | Initially, no seen effect, vomiting 5-6 times a day, effect felt after two weeks with general reduced nausea and vomiting |
| 5 | 1 | Several days | 21 | Reduced nausea |
| 6 | 2 | Extended period | 26 | Reduced nausea, feels much better than in previous pregnancies to the degree of "there is no comparison of how I feel in comparison to previous pregnancies" |
| 7 | 2 | Extended period | 22 | All symptoms of nausea, dehydration, mood swings and vomiting disappeared after 3 days of taking the tablets |
| 8 | 3 | Extended period | Not disclosed | All symptoms of nausea, dehydration, inability to keep the food down and vomiting were reduced by 50% relative to previous pregnancies. |
| 9 | 1 | Several months | 22 | Significant reduction in feelings of nausea |

As can be seen from table 1, the chewable tablets were effective in reducing the general feelings of nausea and reduced vomiting. A large number of other pregnant women tried the chewable tablets and found that their nausea and vomiting was significantly reduced and their general feeling of wellness was improved. Several of the volunteers reported that they felt that they had increased vitality and energy. Some of the volunteers reported better sleeping patterns, but these were not quantified. Additional beneficial effects of the tablets reported were less flatulence and abdominal gases, and improved emotional wellbeing, described as being less irritable.

Volunteer number 1 (Table 1) reported that she was in her fifth pregnancy. During her previous four pregnancies she suffered from prolonged periods of serious vomiting and nausea. She was unable to work and to perform other daily functions. In her fifth pregnancy, she took the tablets twice a day, once in the morning and once in the evening for a period of five weeks. During this pregnancy, she managed to work and function fairly normally. Her vomiting was reduced and the feelings of nausea were significantly reduced during the five weeks of taking the tablets.

Volunteer number 8 (Table 1) reported that she took the tablets during her fifth pregnancy and that she had previously suffered from nausea with all of the previous pregnancies. In her first pregnancy, she was severely dehydrated and could not keep any food down, and was hospitalized in order to receive intravenous fluids. During her first pregnancy, she recalled receiving vitamin B6 injections, which she did not feel helped at the time. She further reported that her second pregnancy was much like the first. Additionally, she mentioned that during her third and fourth pregnancies she learnt how to manage the nausea better and did not require intravenous fluids, but could not escape the feelings of nausea.

As soon as she discovered that she was pregnant for the fifth time, she began taking one tablet a day. When the nausea set in, she increased the dosage to three tablets a day, one after each meal. Volunteer 8 reported that this significantly helped the nausea and gauged the improvement of her condition as being roughly 50%. Volunteer 8 further reported that she was still nauseous, but not incapacitated and was able, with the help of the tablets to take care of her children and did not need to lie in bed all day.

Volunteer number 8 further mentioned that she forgot to take some of the tablets for two days. The following two days were her worst two days of nausea during the pregnancy. Thereafter, she resumed taking the tablets regularly at even intervals during the day—after breakfast, lunch and dinner, and her condition improved again.

Example 5

Reduction of Symptoms of Hangover-Induced Nausea

A 48 year old man, who previously complained of vomiting, headaches during drinking and hangover-induced nausea and headaches "the morning after" and drinking significant quantities of alcohol was provided with tablets, as described in Example 3, hereinabove. He took two to three tablets-a-day for three days prior to the planned drinking event. He reported that at each previous drinking event (without the tablets) in which he had become drunk, he had vomited and was extremely nauseous during and after drinking alcohol.

In sharp contrast, at the event in which he had taken tablets for three days previously, after drinking a similar significant quantity of alcohol, he did not vomit and did not feel at all nauseous.

According to some further embodiments, tablets may be prepared in accordance with Example 3, wherein the vitamin B6 is replaced with a vitamin B complex in quantities of 10 to 500 mg vitamin B complex. In another embodiment the tablet comprises 20 to 300 mg vitamin B complex. In another embodiment the tablet comprises 50 to 200 mg vitamin B complex. In another embodiment the tablet comprises 100 to 150 mg vitamin B complex.

According to some further embodiments, the tablet further comprises folic acid in addition to the vitamin B complex. According to some embodiments, the tablets comprise 50 to 600 micrograms folic acid. According to some embodiments, the tablets comprise 100 to 500 micrograms folic acid. According to some embodiments, the tablets comprise 200 to 400 micrograms folic acid.

It is to be understood that the invention is not limited in its application to the details set forth in the description contained herein. The invention is capable of other embodiments and of being practiced and carried out in various ways. Those skilled in the art will readily appreciate that various modifications and changes can be applied to the embodiments of the invention as hereinbefore described without departing from its scope, defined in and by the appended claims.

What is claimed is:

1. A composition suitable for treating nausea in a subject, wherein said nausea is selected from pregnancy nausea, hangover-associated nausea, alcohol-induced nausea, travel sickness and chemotherapy-associated nausea, the composition comprising vitamins as active ingredients, wherein said active ingredients comprises 10 to 80 mg vitamin B6, 1-10 mcg vitamin K, 2-300 mg vitamin C, and 5-300 mg choline and wherein said composition is in an oral dosage form.

2. A composition suitable for treating nausea in a subject, wherein said nausea is selected from pregnancy nausea, hangover-associated nausea, alcohol-induced nausea, travel sickness and chemotherapy-associated nausea, the composition comprising vitamins as active ingredients, wherein said active ingredients comprises 10 to 80 mg vitamin B6, 1-10 mcg vitamin K, 2-300 mg vitamin C, and 50-400 mg methionine and wherein said composition is in an oral dosage form.

3. The composition of claim 2, comprising 100-400 mg L-methionine.

4. The composition of claim 2, wherein said oral dosage form is a chewable oral dosage form.

5. The composition of claim 2, wherein said active ingredients comprise 60-80 mg vitamin B6, 5-10 mcg vitamin K, and 250-300 mg vitamin C.

6. A composition suitable for treating nausea in a subject, wherein said nausea is selected from pregnancy nausea, hangover-associated nausea, alcohol-induced nausea, travel sickness and chemotherapy-associated nausea, the composition comprising vitamins as active ingredients, wherein said active ingredients comprises 10 to 80 mg vitamin B6, 1-10 mcg vitamin K, 2-300 mg vitamin C, and an ingredient selected from the group consisting of fructose, sorbitol, microcrystalline cellulose, magnesium stearate, or a combination thereof, and wherein said composition is in an oral dosage form.

7. A composition suitable for treating nausea in a subject, wherein said nausea is selected from pregnancy nausea, hangover-associated nausea, alcohol-induced nausea, travel sickness and chemotherapy-associated nausea, the composition comprising vitamins as active ingredients, wherein said active ingredients comprises 10 to 80 mg vitamin B6, 1-10 mcg vitamin K, 2-300 mg vitamin C, and vitamin B complex and wherein said composition is in an oral dosage form.

8. A composition according to claim 7, further comprising folic acid.

9. A composition suitable for preventing nausea in a subject, wherein said nausea is selected from hangover-associated nausea and alcohol-induced nausea, the composition comprising vitamins as active ingredients, wherein said active ingredients comprises 10 to 80 mg vitamin B6, 1-10 mcg vitamin K, 2-300 mg vitamin C, and 5-300 mg choline and wherein said composition is in an oral dosage form.

10. A composition suitable for preventing nausea in a subject, wherein said nausea is selected from hangover-associated nausea and alcohol-induced nausea, the composition comprising vitamins as active ingredients, wherein said active ingredients comprises 10 to 80 mg vitamin B6, 1-10 mcg vitamin K, 2-300 mg vitamin C, and 50-400 mg methionine and wherein said composition is in an oral dosage form.

11. The composition of claim 10, comprising 100-400 mg L-methionine.

12. The composition of claim 10, wherein said oral dosage form is a chewable oral dosage form.

13. The composition of claim 10, wherein said active ingredients comprise 60-80 mg vitamin B6, 5-10 mcg vitamin K, and 250-300 mg vitamin C.

14. A composition suitable for preventing nausea in a subject, wherein said nausea is selected from hangover-associated nausea and alcohol-induced nausea, the composition comprising vitamins as active ingredients, wherein said active ingredients comprises 10 to 80 mg vitamin B6, 1-10 mcg vitamin K, 2-300 mg vitamin C, and any one of fructose, sorbitol, microcrystalline cellulose, magnesium stearate, or a combination thereof and wherein said composition is in an oral dosage form.

15. A composition suitable for preventing nausea in a subject, wherein said nausea is selected from hangover-associated nausea and alcohol-induced nausea, the composition comprising vitamins as active ingredients, wherein said active ingredients comprises 10 to 80 mg vitamin B6, 1-10 mcg vitamin K, 2-300 mg vitamin C, and vitamin B complex and wherein said composition is in an oral dosage form.

16. A composition according to claim 15, further comprising folic acid.

17. The composition of claim 1, wherein said oral dosage form is a chewable oral dosage form.

18. The composition of claim 1, wherein said active ingredients comprise 60-80 mg vitamin B6, 5-10 mcg vitamin K, and 250-300 mg vitamin C.

19. The composition of claim 6, wherein said oral dosage form is a chewable oral dosage form.

20. The composition of claim 6, wherein said active ingredients comprise 60-80 mg vitamin B6, 5-10 mcg vitamin K, and 250-300 mg vitamin C.

21. The composition of claim 7, wherein said oral dosage form is a chewable oral dosage form.

22. The composition of claim 7, wherein said active ingredients comprise 60-80 mg vitamin B6, 5-10 mcg vitamin K, and 250-300 mg vitamin C.

23. The composition of claim 9, wherein said oral dosage form is a chewable oral dosage form.

24. The composition of claim 9, wherein said active ingredients comprise 60-80 mg vitamin B6, 5-10 mcg vitamin K, and 250-300 mg vitamin C.

25. The composition of claim 14, wherein said oral dosage form is a chewable oral dosage form.

26. The composition of claim 14, wherein said active ingredients comprise 60-80 mg vitamin B6, 5-10 mcg vitamin K, and 250-300 mg vitamin C.

27. The composition of claim 15, wherein said oral dosage form is a chewable oral dosage form.

28. The composition of claim 15, wherein said active ingredients comprise 60-80 mg vitamin B6, 5-10 mcg vitamin K, and 250-300 mg vitamin C.

29. A method for preventing or treating nausea in a subject comprising administering orally to said subject a composition comprising vitamin B6, vitamin K, and vitamin C, thereby preventing nausea in a subject, wherein said composition comprises 10 to 80 mg vitamin B6, 1-10 mcg vitamin K, 2-300 mg vitamin C and an ingredient selected from the group consisting of: 5-300 mg choline, 50-400 mg methionine, vitamin B complex and fructose, sorbitol, microcrystalline cellulose, magnesium stearate, or a combination thereof, and wherein said composition is in an oral dosage form and wherein said nausea is selected from pregnancy nausea, hangover-associated nausea, alcohol-induced nausea, travel sickness and chemotherapy-associated nausea.

30. The method of claim 29, wherein said subject is treated with a chemotherapeutic agent.

* * * * *